United States Patent [19]
Xie et al.

[11] Patent Number: 6,110,195
[45] Date of Patent: Aug. 29, 2000

[54] METHOD AND APPARATUS FOR SURGICAL AND DERMATOLOGICAL TREATMENT BY MULTI-WAVELENGTH LASER LIGHT

[75] Inventors: Ping Xie, San Jose; Honghua Qiu, Sunnyvale, both of Calif.

[73] Assignee: Altralight, Inc., Sunnyvale, Calif.

[21] Appl. No.: 09/088,416

[22] Filed: Jun. 1, 1998

[51] Int. Cl.[7] ............................. A61B 18/18; A61N 5/06
[52] U.S. Cl. ................... 607/89; 606/10; 606/11
[58] Field of Search .................... 606/1, 14, 15, 606/16, 10, 11, 12; 607/88, 89, 90

[56] References Cited

U.S. PATENT DOCUMENTS

| | | | |
|---|---|---|---|
| 5,188,633 | 2/1993 | Kratzer et al. | 606/12 |
| 5,249,121 | 9/1993 | Baum et al. | 606/1 |
| 5,390,204 | 2/1995 | Yessik et al. | 606/12 |
| 5,540,676 | 7/1996 | Freiberg | 606/10 |
| 5,634,922 | 6/1997 | Hirano et al. | 606/10 |
| 5,662,644 | 9/1997 | Swor | 606/10 |
| 5,717,806 | 2/1998 | Pileski et al. | 606/16 |
| 5,873,875 | 2/1999 | Altshuler | 606/10 |
| 5,993,442 | 11/1999 | Omori | 606/10 |

*Primary Examiner*—Linda C. M. Dvorak
*Assistant Examiner*—Sonya Harris-Ogugua
*Attorney, Agent, or Firm*—C. P. Chang; Pacific Law Group LLP

[57] ABSTRACT

A method and apparatus for surgical and dermatological treatment using a multi-wavelength laser system includes a primary laser beam generator optically pumped by a semiconductor laser diode. A portion or all of the optical pumping energy may be outputted with the primary laser beam output to form a multi-wavelength treatment beam. A frequency doubling medium, such as a KTP or LBO crystal, may be imposed in the output of the laser beam generator to produce an additional wavelength that may be combined into the multi-wavelength treatment beam. To achieve high peak power pulse laser output, a Q-switch element can be placed in front or in back of the laser crystal. Alternatively, the laser system may output only the wavelength of the semiconductor laser diode pumping system. The selection of one or more wavelengths provides a wider range of treatment modalities using a single laser system, without creating problems attendant with the complexity and maintenance of prior art multi-wavelength laser systems. The laser system may include a plurality of laser diodes, each arranged to generate an output at a respective unique wavelength. The laser diode outputs are combined in a beam mixer and directed through a fiberoptic delivery system to a surgical handpiece or the like. The laser diodes are operated individually to provide a combination of wavelengths of laser light that may be adjusted continuously in CW mode or pulse mode to create varying thermal effects for different treatment modalities.

10 Claims, 5 Drawing Sheets

METHOD AND APPARATUS FOR SURGICAL AND DERMATOLOGICAL TREATMENT BY MULTI-WAVELENGTH LASER LIGHT

BACKGROUND OF THE INVENTION

This invention relates to therapeutic treatment of the epidermis, and more particularly to the use of lasers for surgical and dermatological treatment.

In recent years there has been significant growth in the use of lasers to treat epidermal conditions, such as vascular and pigmented lesions, tattoo removal, depilation, and the like. A variety of laser systems have been developed for these applications, many being based on the premise that the various constituents of the epidermis have widely varying absorption characteristics of different wavelengths of light. For example, hemoglobin, a primary light absorber in blood, has a peak absorption function between $0.4\mu$–$0.5\mu$, whereas water constituents have a minimal absorption at this wavelength range. Thus laser systems for treating vascular lesions are designed to operate in this range. In contrast, water, a basic component of soft tissue, has a peak absorption characteristic at about $3\mu$. Tattoo dyes have varying absorption characteristics, based on their color. Melanin, a primary pigment, is concentrated in pigmented lesions and hair, and has good absorption in the range of $0.3\mu$–$1.0\mu$. A laser system operating in the $0.6\mu$–$1.0\mu$ range can treat pigmented lesions and carry out depilation while avoiding significant absorption by hemoglobin.

Thus it is clear that the wavelength of laser light is a critical factor in determining which epidermal structures are selectively affected, and which are unscathed by the treatment. Most laser systems generate only one wavelength, and are therefore limited to treating only one or a limited number of epidermal conditions. The limited usage of a laser system, which is often an expensive item, can limit its viability as a medical instrument, due to the economic realities of modern medicine.

Multi-wavelength laser system have been devised to overcome such limitations in usage. For example, tunable dye lasers can generate a wide range of wavelengths, depending on the dye being used and the configuration of the resonant cavity. However, dye lasers are extremely complex and expensive, and difficult to maintain. The dye solution must be renewed frequently, and the systems for circulating and cooling the dye solution can become maintenance and operating difficulties.

Another technique for achieving multi-wavelength operation is the use of a frequency conversion medium. For example, a KTP or LBO optical crystal can double the frequency of a laser beam, resulting in an output that has one-half the wavelength of the incident laser beam. There is a substantial loss of output power in these systems, necessitating a far larger laser system with its attendant cost and maintenance. Furthermore, these optical crystals are generally limited to frequency doubling, thereby limiting the selection of output wavelengths to a few choices based to the choices of lasing mediums.

Some dermatology treatment systems use a broadband light source to provide actinic radiation, rather than a laser light source. Such systems are expensive, they do not provide the selectivity of monochromatic light, nor the ability to be focused into a narrow and supple optical fiber for convenient delivery to the treatment site.

There is clearly a need for a multi-wavelength laser system that can accomplish a wide range of dermatology and surgical procedures and provide cost-effective treatment.

SUMMARY OF THE INVENTION

The present invention generally comprises a method and apparatus for surgical and dermatological treatment using selected wavelengths of the output of a multi-wavelength output laser system.

In one aspect, the invention includes a laser system having a primary laser beam generator optically pumped by a semiconductor laser diode. The system includes means for outputting a portion or all of the optical pumping energy and combining that pumping wavelength with the primary laser beam generator output to form a multi-wavelength treatment beam. In addition, a frequency doubling medium, such as a KTP or LBO crystal, may be imposed in the output of the laser beam generator to produce an additional wavelength that may be combined into the multi-wavelength treatment beam. Alternatively, the laser system may output only the wavelength of the semiconductor laser diode pumping system. The selection of one or more wavelengths provides a wider range of treatment modalities using a single laser system, without creating problems attendant with the complexity and maintenance of prior art multi-wavelength or tunable laser systems.

In a further aspect, the invention includes a laser system in which a primary laser beam generator is provided with an optical pumping input connector and a treatment beam output connector, an optical pumping source is provided with an output port. An optical fiber delivery system includes an output end arranged to deliver the treatment beam to a tissue treatment site, and an input connector that may be removably connected to the primary laser beam generator output connector, and a jumper fiberoptic may be connected between the optical pumping source output connector and the input connector of the primary laser beam generator. Thus the treatment beam may comprise a multi-wavelength combination of the pumping source wavelength and the primary laser beam wavelength. Alternatively, the jumper fiberoptic may be removed, and the optical fiber delivery system may be connected directly to the output connector of the optical pumping source to deliver the single wavelength of the pumping source as a treatment beam.

In an additional aspect of the invention, the laser systems described above are provided with an internal reflection arrangement that delivers a portion of the optical pumping energy to the primary laser beam generator, and the remainder of the optical pumping energy is directed to the treatment beam output connector where it is combined with the primary laser beam output to comprise a multi-wavelength treatment beam.

In another aspect of the invention, a laser system is comprised of a plurality of semiconductor laser diodes, each arranged to generate a laser beam output at a respective unique wavelength. The laser beam outputs are connected to a respective plurality of optical fibers. The optical fibers are combined in a beam mixer and directed through a fiberoptic delivery system to a surgical handpiece or the like. Alternatively, the laser beam outputs of the laser diodes may be directed to respective mirrors and combined at a beam mixer output connector. In either case, the laser diodes are operated individually to provide a combination of wavelengths of laser light that may be adjusted continuously. For example, the power of each laser diode may be selected to vary the continuous wave mix, or the individual laser diodes may be controlled in a pulse mode to create varying pulse sequences to create varying thermal effects for different treatment modes.

In all of these aspects, the laser system includes a power supply, a thermoelectric cooling system for the optical pumping source, a control system for operating the power supply, and a display to indicate the treatment beam wavelengths, duration, power, and accumulated energy delivered to the treatment site. In addition, the output end of the delivery system may comprise a handpiece for directing the treatment beam manually, or a computer controlled pattern generator, as described in copending U.S. patent application Ser. No. 09/024,437, filed Feb. 17, 1998 by the present inventor and incorporated herein by reference.

DESCRIPTION OF THE PREFERRED EMBODIMENT

The present invention generally comprises a method and apparatus for epidermal treatment and the like using selected wavelengths of the output of a multi-wavelength output laser system. The method and apparatus are described herein with reference to treatment of vascular and pigmented lesions, tattoo removal, depilation, and other dermatological and surgical procedures, although other treatment modalities and conditions susceptible to multi-wavelength laser light may also be carried out.

Figure 1:
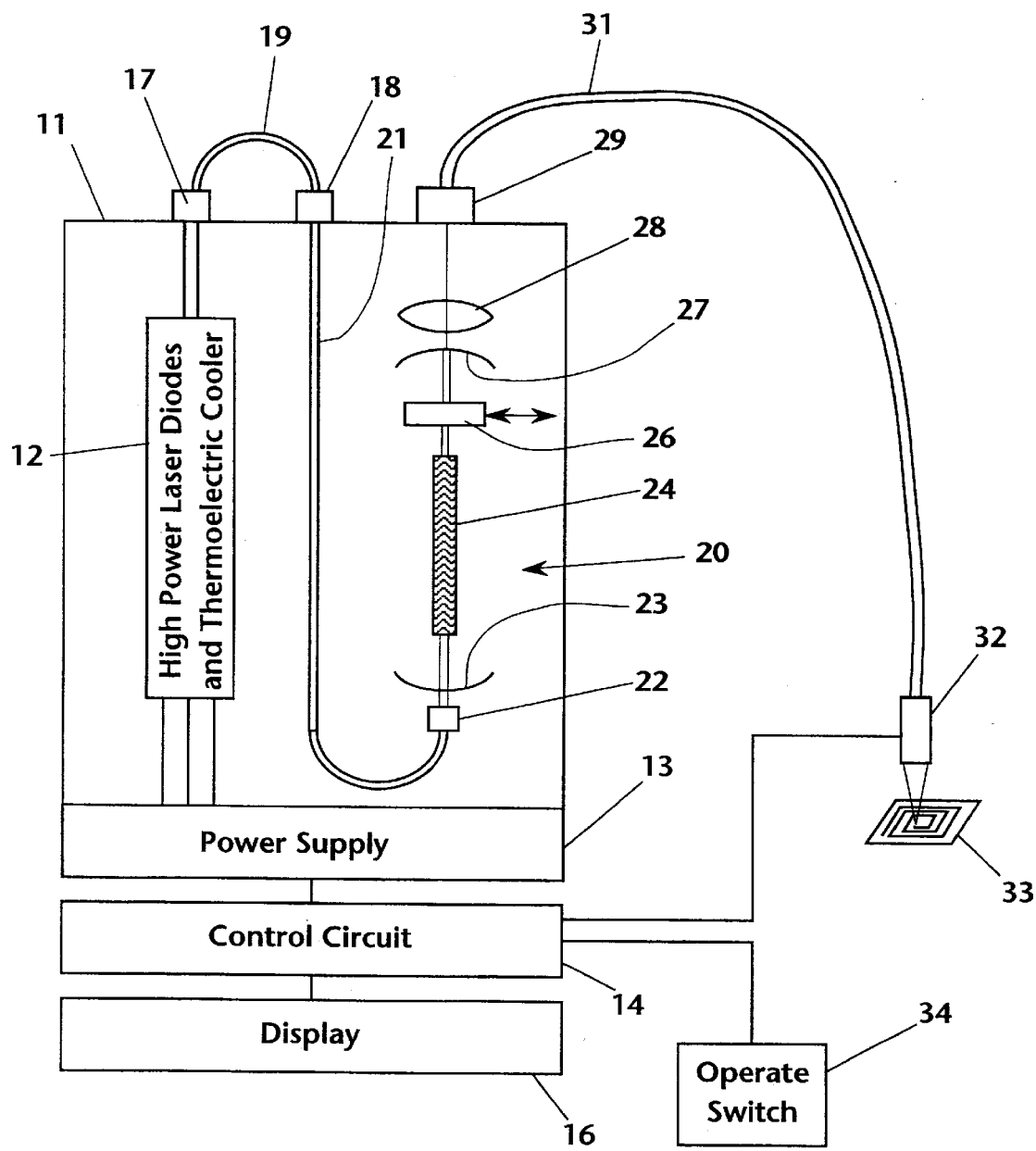
FIG. 1 is a functional block diagram of the multi-wavelength laser system of the present invention, shown in one output configuration.

With reference to FIG. 1, one embodiment of the apparatus of the invention includes an enclosure 11 in which a high power laser diode array 12 is supported, the array 12 including a cooling system comprising a thermoelectric heat transfer system, as is known in the prior art. The system includes a controlled power supply 13 capable of driving the laser diode array 12 in continuous wave or pulsed operation, and providing a selectively variable instantaneous output power level from the laser diode array 12. A control circuit 14 is connected to the power supply and to an operator display 16, the control circuit governing the parameters enumerated hereinafter, and the display indicating the state of operation of the system 11, including output power level, pulse or CW operation, total joules delivered, wavelengths produced, wavelength ratio, operating faults or safety messages, and the like.

The output of the laser diode array 12 is directed to an external optical fiber connector 17, such as an industry standard SMA connector or the like. A similar optical fiber connector 18 is also provided, and is connected internally to an optical fiber or waveguide 21. An optical fiber 19 may be connected between the connectors 17 and 18. A primary laser beam generator is also supported within the apparatus 11, including a laser crystal rod 24 bracketed by a pair of mirrors 23 and 27 to form a resonant laser cavity. The optical fiber 21 is connected to a fixture 22 which directs the output of laser diode array 12 through the mirror 23 to the laser rod 24. As is known in the prior art, the output of the laser diode array 12 optically pumps the crystalline material of the laser rod 24 to stimulate the emission of coherent radiation therefrom. The output beam of the primary laser generator passes through the mirror 27 to the lens 28, which focuses the primary laser beam at another external optical fiber connector 29.

An optical fiber delivery system 31 is joined at one end to the connector 29 to receive the laser beam from the laser rod 24. At the distal end, the delivery system 31 is provided with a handpiece 32 designed to output the laser energy in a manner that is optimal for the procedure being carried out. For example, the handpiece 32 may comprise a scanner device for directing the beam in a pattern 33 that provides a desired disbursement of the laser radiance to a target surface. In this case, the scanner, which may comprise a computer controlled pattern generator, may be driven by the control circuit 14. Likewise, the handpiece 32 may contain focusing optics to create a high energy density for ablation and the like, or defocusing optics for a broad dispersal of the laser energy.

In the configuration depicted in FIG. 1, the output of the laser system comprises primarily the output of the primary laser beam generator. Some of the optical pumping energy of the laser diode array 12 may be included, although such wavelengths may be filtered from the output if necessary. In addition, a non-linear optical crystal 26, such as a frequency doubling KTP or LBO material, may be interposed in the beam path of the primary laser beam generator to provide an output having a wavelength equal to one-half of the resonant wavelength of the laser crystal rod 24. The crystal 26 may be interposed or removed by any mechanical actuator. Note that some components commonly used in the prior art, such as focusing optics for inserting laser beams into the various connectors, and the like, are not shown for purposes of clarity in describing the invention.

Figure 2:
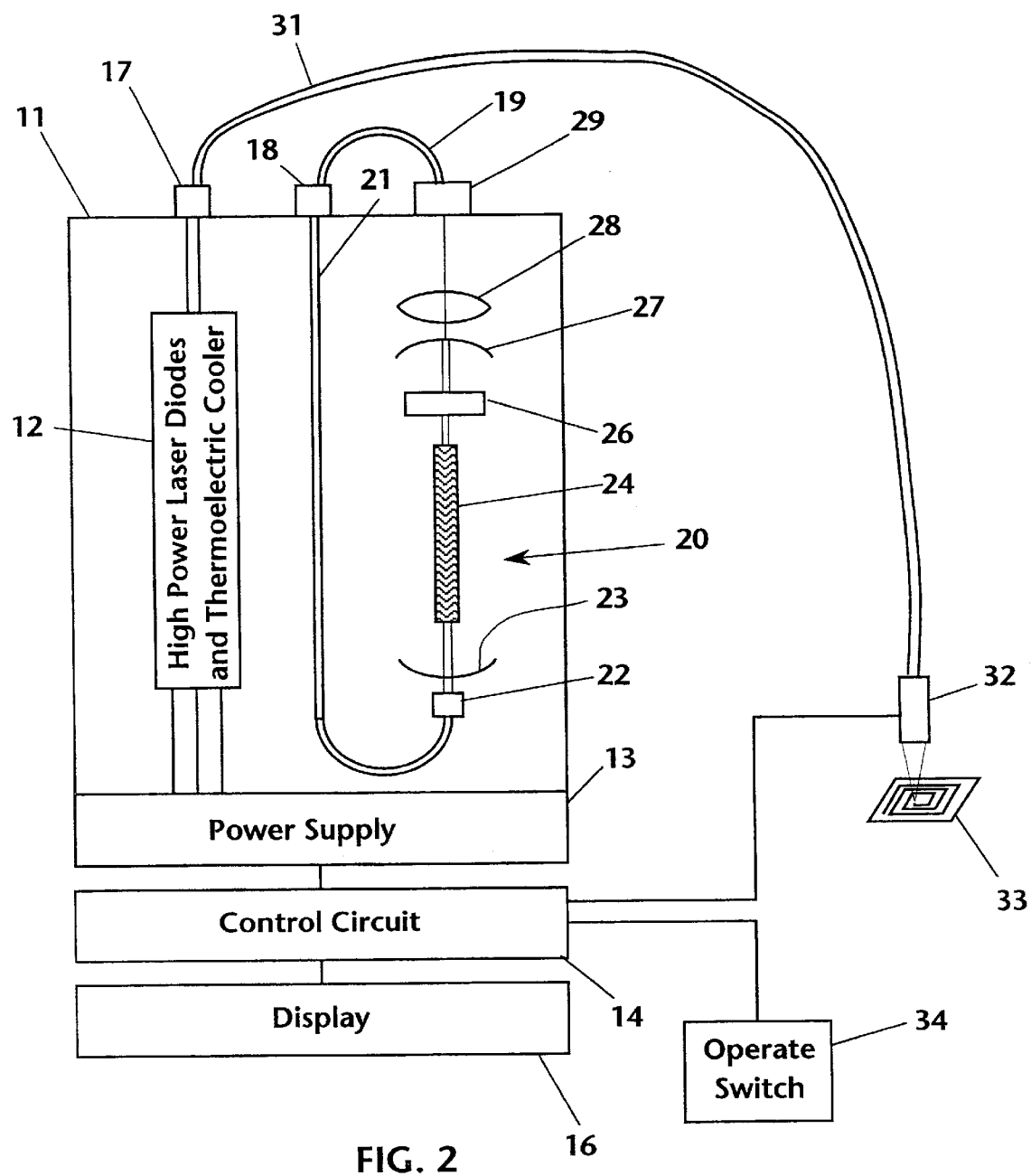
FIG. 2 is a functional block diagram of the multi-wavelength laser system of FIG. 1, shown in another output configuration.

The laser system depicted in FIG. 1 may be reconfigured, as shown in FIG. 2, to provide an output having a different wavelength that is optimized for particular procedures. The optical fiber jumper 19 may be removed from its connection between connectors 17 and 18, and the input end of optical fiber delivery system 31 is joined to connector 17. Thus the output of laser diode array is connected directly to the output handpiece 32, where it may be utilized as described previously to provide different effects. For example, if the laser rod 24 comprises an Nd:YAG crystal, the output of the configuration shown in FIG. 1 is 1.064 $\mu$, and this wavelength is very useful for accomplishing hemostasis of wounds, or for treating vascular lesions by coagulating the blood in the vessels that define the lesion. Further assuming that the laser diode array provides an output in the range of 600 $\mu$–900 $\mu$, this wavelength is very useful for treatment of pigmented lesions and depilation, and the configuration shown in FIG. 2 may be used advantageously for such purposes. Other combinations of laser diode array wavelengths and laser crystal rod wavelengths may be selected by choosing diodes and laser rod materials having desired wavelength characteristics known in the prior art. The laser system shown in FIGS. 1 and 2 thus provides far greater utility than single output lasers known in the prior art, without any substantial increase in the complexity of the system. In addition, the interposition of the non-linear optical crystal 26 further enhances and broadens the wavelength selection provided by the invention. In order to achieve high peak power pulsed laser output, a Q-switch element can be placed in front or in back of laser crystal 24, as is known in the prior art.

Figure 3:
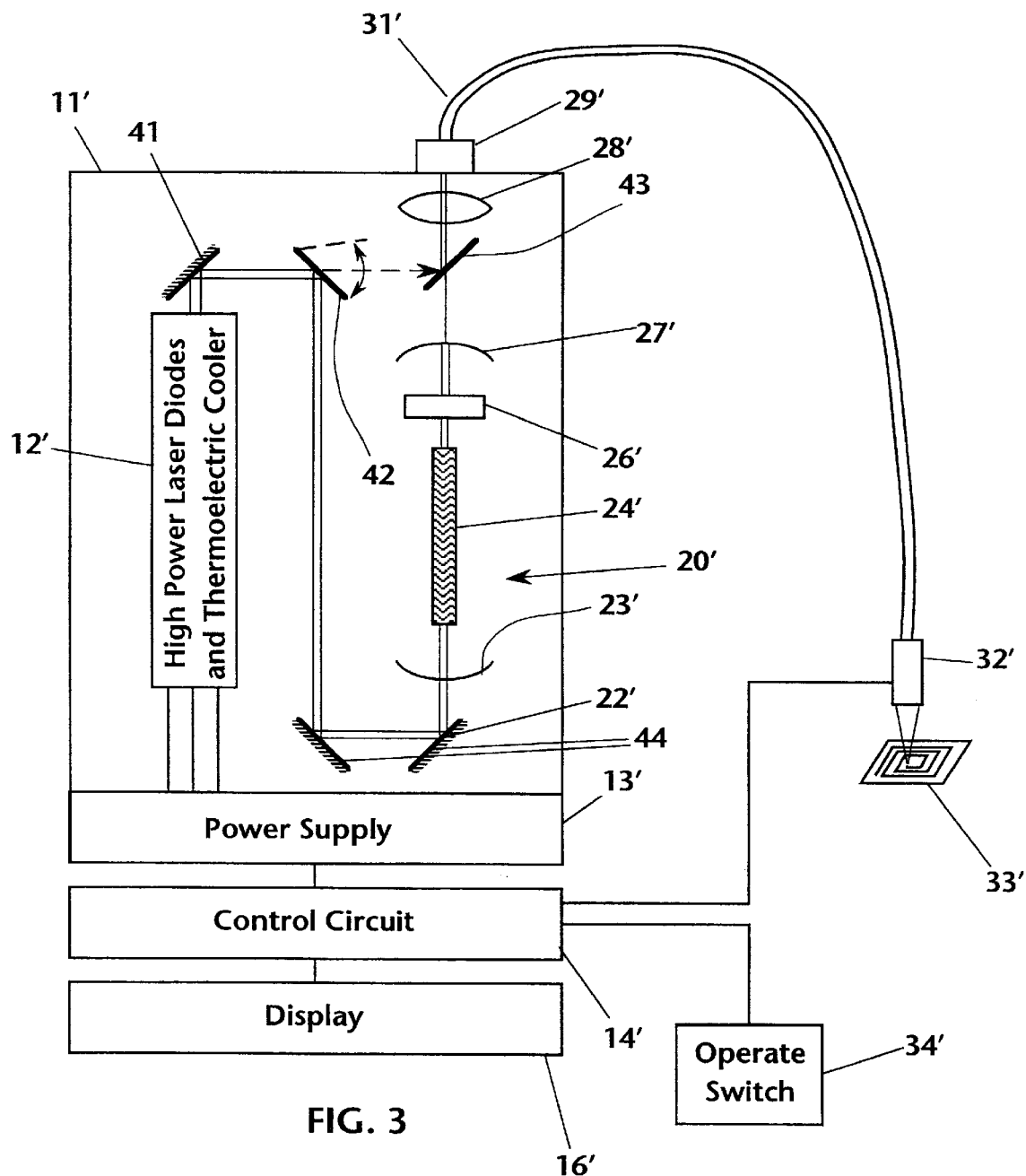
FIG. 3 is a functional block diagram of a further embodiment of the multi-wavelength laser system of the present invention.

With regard to FIG. 3, a further embodiment of the invention includes some components substantially similar to the configuration of FIGS. 1 and 2 and provided with like reference numerals having a prime (') designation. The laser system 11' includes a laser diode array 12' supported therein, as well as the primary laser beam generator comprised of the laser rod 24', mirrors 23' and 27', and associated components. The output of the laser diode array 12' is directed to a fixed mirror 41, which in turn directs the beam to a partially reflective, movable mirror 42. The mirror 42 may be moved (e.g., rotated) to a first position in which the reflected beam is directed to dichroic mirror 43, as shown by the broken line arrow, in which case the diode laser beam is directed through the focusing lens 28, to be inserted into optical fiber 31' secured in connector 29'.

Alternatively, the mirror 42 may be moved to direct the output of laser diode array 12' toward a mirror combination 44 that guides the laser energy into laser rod 24', where it acts as optical pumping energy for the primary laser beam generator. The output of the primary laser beam generator 20' passes through the dichroic mirror 43 which passes the primary laser output while also reflecting the wavelength of laser diode array 12', whereby the two wavelengths are selected and directed through the external connector 29' in accordance with the position of mirror 42. The optical fiber delivery system 31' may be joined to the connector 29' to provide the selected wavelengths to the handpiece 32', as described previously.

Thus the laser system 11' of FIG. 3 may be configured to deliver the laser diode wavelength solely or in combination with the wavelength of the primary laser beam generator 20'. As explained above, the control circuit may operate the laser diode array 12' in CW or pulsed mode, and may also operate an automatic actuator to move the mirror 42 between the two reflective positions described. The use of a jumper connector, such as optical fiber 19, is obviated, and reconfiguration may be carried out without manual intervention in moving optical cables (an optical fiber delivery system may be joined to both connectors 18' and 29'). In addition, a non-linear optical crystal 26' may be included and automatically interposed or removed from the primary laser beam generator to further multiply the number of wavelengths delivered at the output connector 29'.

Figure 4:
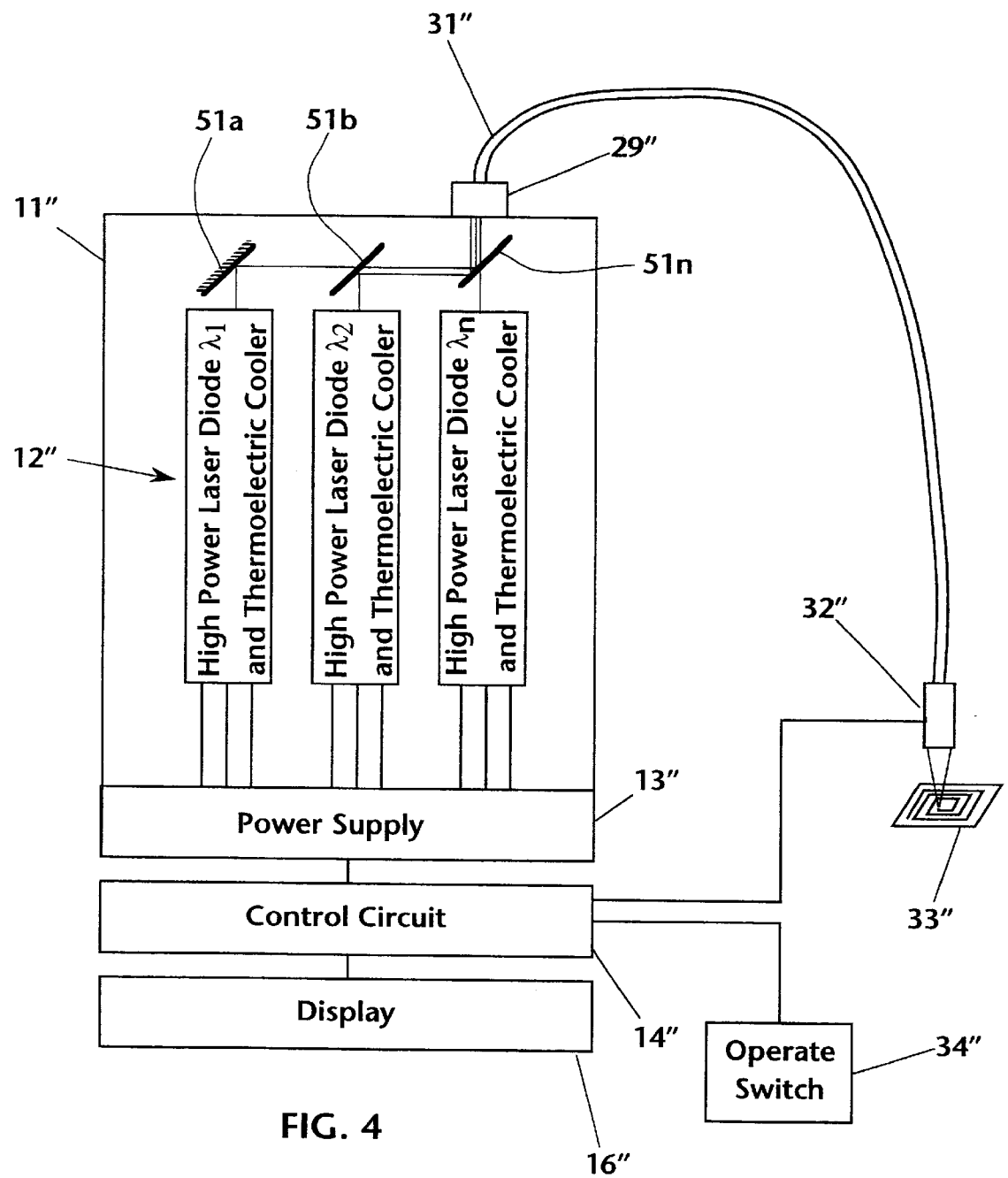
FIG. 4 is a functional block diagram of another embodiment of the multi-wavelength laser system of the present invention.

With regard to FIG. 4, a further embodiment of the invention includes some components substantially similar to the configuration of FIGS. 1–3 and provided with like reference numerals having a double prime (") designation. The laser system 11" includes a plurality 12" of laser diode arrays $\lambda_1$, $\lambda_2$, ... $\lambda_n$ supported therein as described previously. The output of each laser diode array is directed to a respective mirror $51_a$, $51_b$ ... $51_n$, whereby all of the outputs are combined by mirror $^{51}$n and directed to the external connector 29" and thence to the optical fiber delivery system 31". The laser diode arrays $\lambda_1$, $\lambda_2$, ... $\lambda_n$ are driven by the power supply 13" connected to the control circuit 14", which is programmed to operate each of the laser diode arrays individually or in any subset combination, either in CW or pulsed modes.

The control circuit 14" may operate the laser diode arrays 12" (or any subset thereof) in continuous or pulsed fashion to provide a continuous or pulsed output comprised of any selected mix of the individual wavelengths. These temporal or continuous mixes are selectively variable without requiring any manual reconfiguration of the laser system, whereby switching between any possible mix may be accomplished virtually instantaneously. Thus, for example, the wavelength mix may be optimized for treatment of a particular color of pigmented epidermal lesion, or for depilation of a particular hair color. Other possible uses for such selectively variable wavelength mixes may be apparent to individuals skilled in the art.

Figure 5:
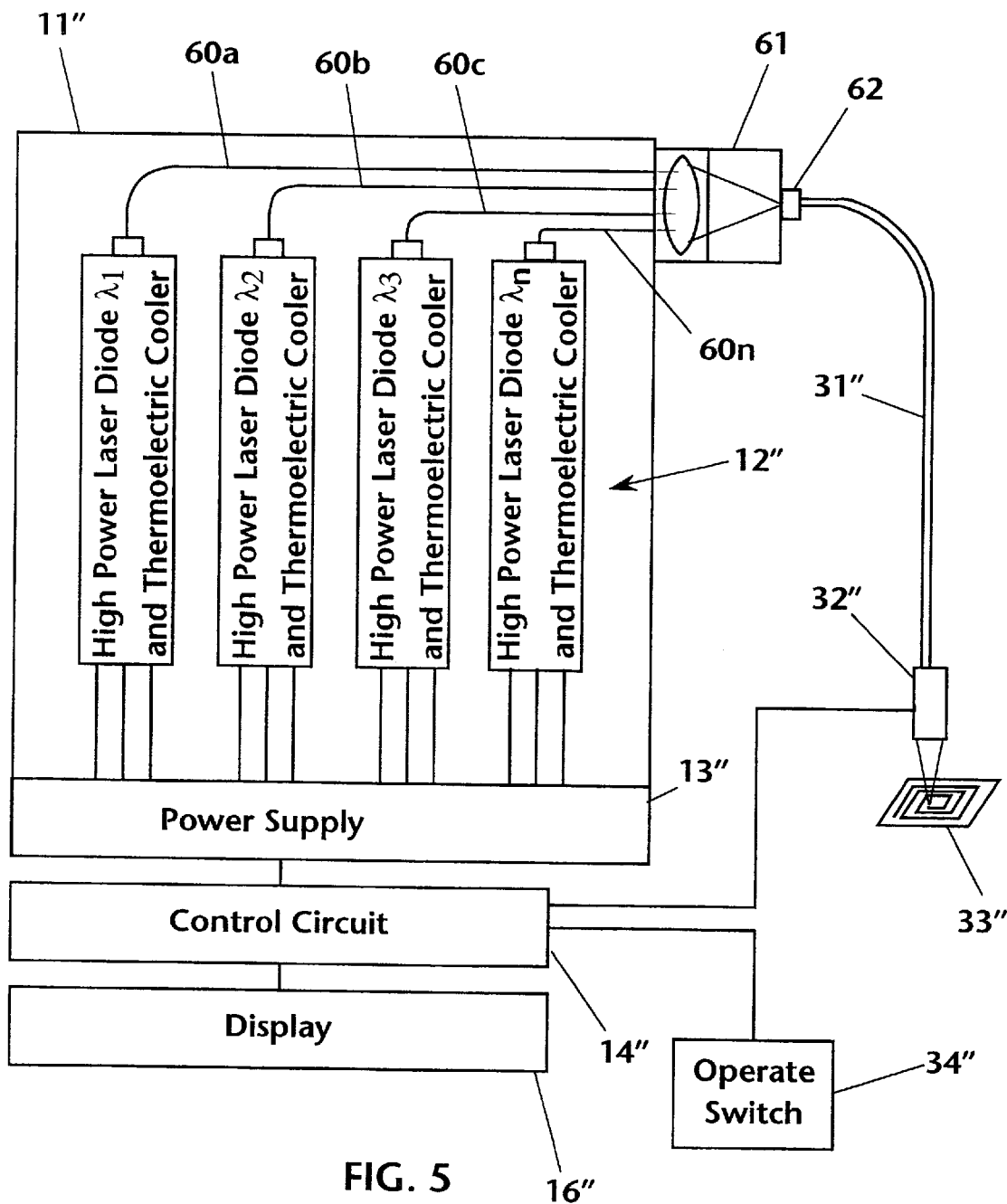
FIG. 5 is a functional block diagram of an additional embodiment of the multi-wavelength laser system of the present invention.

With regard to FIG. 5 a further embodiment of the invention includes some components substantially similar to the configuration of FIG. 4 and provided with like reference numerals having a double prime (") designation. The laser system 11" includes a plurality 12" of laser diode arrays $\lambda_1$, $\lambda_2$, ... $\lambda_n$, supported therein as described previously. The output of each laser diode array is directed to a respective optical fiber 60a, 60b, ... 60n. The output ends of the optical fibers 60 are joined into a bundle and connected to a laser beam combining device 61 which focuses the combined beams into an external connector 62. The optical fiber delivery system 31" is joined to connector 62 to illuminate the handpiece 32", as described previously. The arrangement of FIG. 5 provides all of the functionality and advantages of the system depicted in FIG. 4, while obviating the need to select appropriate passband or coating materials for the mirrors 51 and to maintain the mirror alignments.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

What is claimed is:

1. A laser apparatus, including:

primary laser generator means for generating a first laser output at a first wavelength, said primary laser generator means being optically pumped;

laser diode means for generating a second laser output at a second wavelength, said second wavelength being capable of optically pumping said primary laser generator means;

delivery means for directing the output of said laser apparatus to a target for carrying out useful work;

means for reconfiguring said laser apparatus from a first arrangement in which said delivery means is connected to the output of said primary laser generator means and said laser diode means is connected to optically pump said primary laser generator means, to a second arrangement in which said delivery means is connected to the output of said laser diode means.

2. The laser apparatus of claim 1, wherein said means for reconfiguring said laser apparatus includes a first output connector means for directing the output of said primary laser generator means, said delivery means being releasably securable to said first output connector means.

3. The laser apparatus of claim 2, wherein said means for reconfiguring said laser apparatus includes a second output connector means for directing the output of said laser diode means, said delivery means being releasably securable to said second output connector means.

4. The laser apparatus of claim 3, wherein said means for reconfiguring said laser apparatus includes a third connector means for directing laser energy to said primary laser generator means in optical pumping fashion, and a jumper optical fiber releasably connectable between said second and third connector means for directing the second laser output to said primary laser generator means for optical pumping purposes.

5. The laser apparatus of claim 1, further including a non-linear frequency doubling optical crystal, and means for selectively interposing said optical crystal in a beam path of said primary laser generator means.

6. The laser apparatus of claim 1, wherein said delivery means includes an output device incorporating a computer controlled pattern generator for directing the output of said laser apparatus to trace selected patterns on the target.

7. The laser apparatus of claim 2, wherein said means for reconfiguring said laser apparatus includes mirror means for reflecting the output of said laser diode means to said primary laser generator means in optical pumping fashion.

8. The laser apparatus of claim 7, wherein said mirror means includes a movable mirror that is movable between a first position in which the output of said laser diode means is directed to said primary laser generator means, to a second position in which the output of said laser diode means is directed to said first output connector means.

9. The laser apparatus of claim 1, further including control means for operating said laser diode means in continuous wave fashion.

10. The laser apparatus of claim 1, further including control means for operating said laser diode means in pulsed mode.

* * * * *